United States Patent
Kang et al.

(10) Patent No.: US 10,383,628 B2
(45) Date of Patent: Aug. 20, 2019

(54) SURGICAL LINEAR STAPLER

(71) Applicant: MEDI TULIP CO., Ltd, Cheongju-si, Chungcheongbuk-do (KR)

(72) Inventors: Min Woong Kang, Daejeon (KR); Tae Woong Kang, Daejeon (KR)

(73) Assignee: MEDI TULIP CO., LTD, Cheongju-si, Chungcheongbuk-do (KR)

( * ) Notice: Subject to any disclaimer, the term of this patent is extended or adjusted under 35 U.S.C. 154(b) by 305 days.

(21) Appl. No.: 15/110,943

(22) PCT Filed: Mar. 17, 2016

(86) PCT No.: PCT/KR2016/002730
§ 371 (c)(1),
(2) Date: Jul. 12, 2016

(87) PCT Pub. No.: WO2016/171395
PCT Pub. Date: Oct. 27, 2016

(65) Prior Publication Data
US 2017/0055991 A1    Mar. 2, 2017

(30) Foreign Application Priority Data

Apr. 20, 2015  (KR) .................. 10-2015-0055272
Dec. 8, 2015   (KR) .................. 10-2015-0174204

(51) Int. Cl.
*A61B 17/072*    (2006.01)
*A61B 90/92*     (2016.01)
(Continued)

(52) U.S. Cl.
CPC ...... *A61B 17/072* (2013.01); *A61B 17/07207* (2013.01); *A61B 90/92* (2016.02);
(Continued)

(58) Field of Classification Search
CPC .......... A61B 2017/07278; A61B 2017/07228; A61B 17/068; A61B 17/072;
(Continued)

(56) References Cited

U.S. PATENT DOCUMENTS 4,319,576 A * 3/1982 Rothfuss .............. A61B 17/115
                                              227/175.3
4,442,964 A * 4/1984 Becht ................... A61B 17/072
                                              227/155
(Continued)

FOREIGN PATENT DOCUMENTS

CN    103169517 A    6/2013
EP      1964526 A2   9/2008
(Continued)

OTHER PUBLICATIONS

International Search Report for PCT/KR2016/002730 dated Jul. 25, 2016 from Korean Intellectual Property Office.
(Continued)

*Primary Examiner* — Robert F Long
(74) *Attorney, Agent, or Firm* — Revolution IP, PLLC

(57) ABSTRACT

Disclosed is a surgical linear stapler comprising: a staple cartridge which is internally loaded with staples for stapling a surgical site; a cartridge accommodating channel which is formed with a cartridge accommodating groove to accommodate the staple cartridge therein; an anvil which corresponds to the staple cartridge and shapes the staple discharged from the staple cartridge; and a cutter which moves along a lengthwise direction of the staple cartridge by external force and cuts a surgical site arranged in between the staple cartridge and the anvil, in which distances from the cutting section of the surgical site to opposite stapling lines are different from each other, thereby stably and
(Continued)

conveniently obtaining tissue for pathological examination, which is not damaged by a staple.

16 Claims, 9 Drawing Sheets

(51) Int. Cl.
  *A61B 10/02*    (2006.01)
  *A61B 17/064*    (2006.01)
  *A61B 90/00*    (2016.01)

(52) U.S. Cl.
  CPC .......... *A61B 10/02* (2013.01); *A61B 17/0644* (2013.01); *A61B 2017/07228* (2013.01); *A61B 2017/07235* (2013.01); *A61B 2017/07242* (2013.01); *A61B 2017/07257* (2013.01); *A61B 2017/07271* (2013.01); *A61B 2017/07285* (2013.01); *A61B 2090/0807* (2016.02)

(58) Field of Classification Search
  CPC ........ A61B 17/105; A61B 2017/07264; A61B 10/02; A61B 90/92; A61B 17/07207; A61B 2090/0807; A61B 2017/07235; A61B 17/0644; A61B 2017/07285; A61B 2017/07271; A61B 2017/07257; A61B 2017/07242
  USPC ............ 606/139, 142, 143; 227/175.1–182.1
  See application file for complete search history.

(56) References Cited

U.S. PATENT DOCUMENTS

| | | | |
|---|---|---|---|
| 4,527,724 A * | 7/1985 | Chow ................... | A61B 17/072 227/8 |
| 4,848,637 A * | 7/1989 | Pruitt ................... | A61B 17/072 227/19 |
| 5,308,576 A * | 5/1994 | Green ................ | A61B 17/07207 227/175.1 |
| 5,364,003 A * | 11/1994 | Williamson, IV ... | A61B 17/072 227/178.1 |
| 5,441,191 A * | 8/1995 | Linden ................ | B25C 5/1689 227/120 |
| 5,507,425 A * | 4/1996 | Ziglioli ................ | B25C 5/1689 116/278 |
| 5,560,530 A * | 10/1996 | Bolanos ........... | A61B 17/07207 227/176.1 |
| 5,582,611 A * | 12/1996 | Tsuruta ............ | A61B 17/00234 606/142 |
| 5,709,335 A * | 1/1998 | Heck .................... | A61B 17/115 227/176.1 |
| 5,876,401 A * | 3/1999 | Schulze ........... | A61B 17/07207 606/51 |
| H1904 H * | 10/2000 | Yates ........................... | 606/142 |
| 6,383,958 B1 * | 5/2002 | Swanson ............. | A61F 13/0269 442/151 |
| H2037 H * | 7/2002 | Yates ............................... | 606/51 |
| 8,021,375 B2 | 9/2011 | Aldrich et al. | |
| 10,092,292 B2 * | 10/2018 | Boudreaux ....... | A61B 17/07207 |
| 10,130,359 B2 * | 11/2018 | Hess ....................... | F16B 15/00 |
| 10,136,888 B2 * | 11/2018 | Chen .................. | A61B 17/1155 |
| 2004/0232197 A1 * | 11/2004 | Shelton, IV ..... | A61B 17/07207 227/175.1 |
| 2006/0016853 A1 * | 1/2006 | Racenet ............... | A61B 17/068 227/176.1 |
| 2006/0219752 A1 * | 10/2006 | Arad ................ | A61B 17/07207 227/176.1 |
| 2009/0048589 A1 * | 2/2009 | Takashino ........ | A61B 17/07207 606/28 |
| 2009/0065552 A1 * | 3/2009 | Knodel ................ | A61B 17/072 227/180.1 |
| 2009/0114701 A1 * | 5/2009 | Zemlok ................ | A61B 17/064 227/176.1 |
| 2009/0177201 A1 * | 7/2009 | Soltz .................. | A61B 17/0644 606/75 |
| 2009/0206144 A1 * | 8/2009 | Doll ................ | A61B 17/07207 227/177.1 |
| 2010/0108741 A1 * | 5/2010 | Hessler ............... | A61B 17/1114 227/179.1 |
| 2010/0213240 A1 * | 8/2010 | Kostrzewski ........ | A61B 17/072 227/180.1 |
| 2010/0320252 A1 * | 12/2010 | Viola ............... | A61B 17/07207 227/176.1 |
| 2011/0036891 A1 * | 2/2011 | Zemlok ............ | A61B 17/07207 227/176.1 |
| 2011/0068147 A1 * | 3/2011 | Racenet ............... | A61B 17/072 227/180.1 |
| 2011/0089221 A1 * | 4/2011 | Masiakos ......... | A61B 17/07207 227/180.1 |
| 2012/0145768 A1 * | 6/2012 | Sorrentino ....... | A61B 17/07207 227/181.1 |
| 2013/0082086 A1 * | 4/2013 | Hueil ............... | A61B 17/07207 227/177.1 |
| 2013/0334284 A1 * | 12/2013 | Swayze ............. | A61B 17/0682 227/180.1 |
| 2014/0103092 A1 | 4/2014 | Kostrzewski et al. | |
| 2014/0203061 A1 | 7/2014 | Hodgkinson | |
| 2014/0263551 A1 | 9/2014 | Hall et al. | |
| 2014/0374464 A1 | 12/2014 | Viola et al. | |
| 2015/0150620 A1 * | 6/2015 | Miyamoto ....... | A61B 17/07207 606/51 |
| 2015/0173762 A1 * | 6/2015 | Shelton, IV ....... | A61B 17/0644 227/177.1 |
| 2015/0289872 A1 * | 10/2015 | Chen .................. | A61B 17/1155 227/179.1 |
| 2015/0297233 A1 * | 10/2015 | Huitema ............. | A61B 17/068 227/176.1 |
| 2017/0020525 A1 * | 1/2017 | Shah ................ | A61B 17/07207 |
| 2017/0027569 A1 * | 2/2017 | Scheib .............. | A61B 17/07207 |
| 2017/0105728 A1 * | 4/2017 | Scheib ................ | A61B 17/068 |
| 2017/0105731 A1 * | 4/2017 | Scheib ................ | A61B 17/068 |
| 2017/0367697 A1 * | 12/2017 | Shelton, IV ......... | A61B 17/068 |
| 2018/0168632 A1 * | 6/2018 | Harris .............. | A61B 17/07207 |

FOREIGN PATENT DOCUMENTS

| | | |
|---|---|---|
| EP | 2777531 A1 | 9/2014 |
| JP | 2001-145632 A | 5/2001 |
| JP | 2014-079608 A | 5/2014 |
| JP | 2014-140746 A | 8/2014 |

OTHER PUBLICATIONS

European Search Report for EP Application No. 16 783 329.2 dated Aug. 3, 2017 from European Patent Office.

* cited by examiner

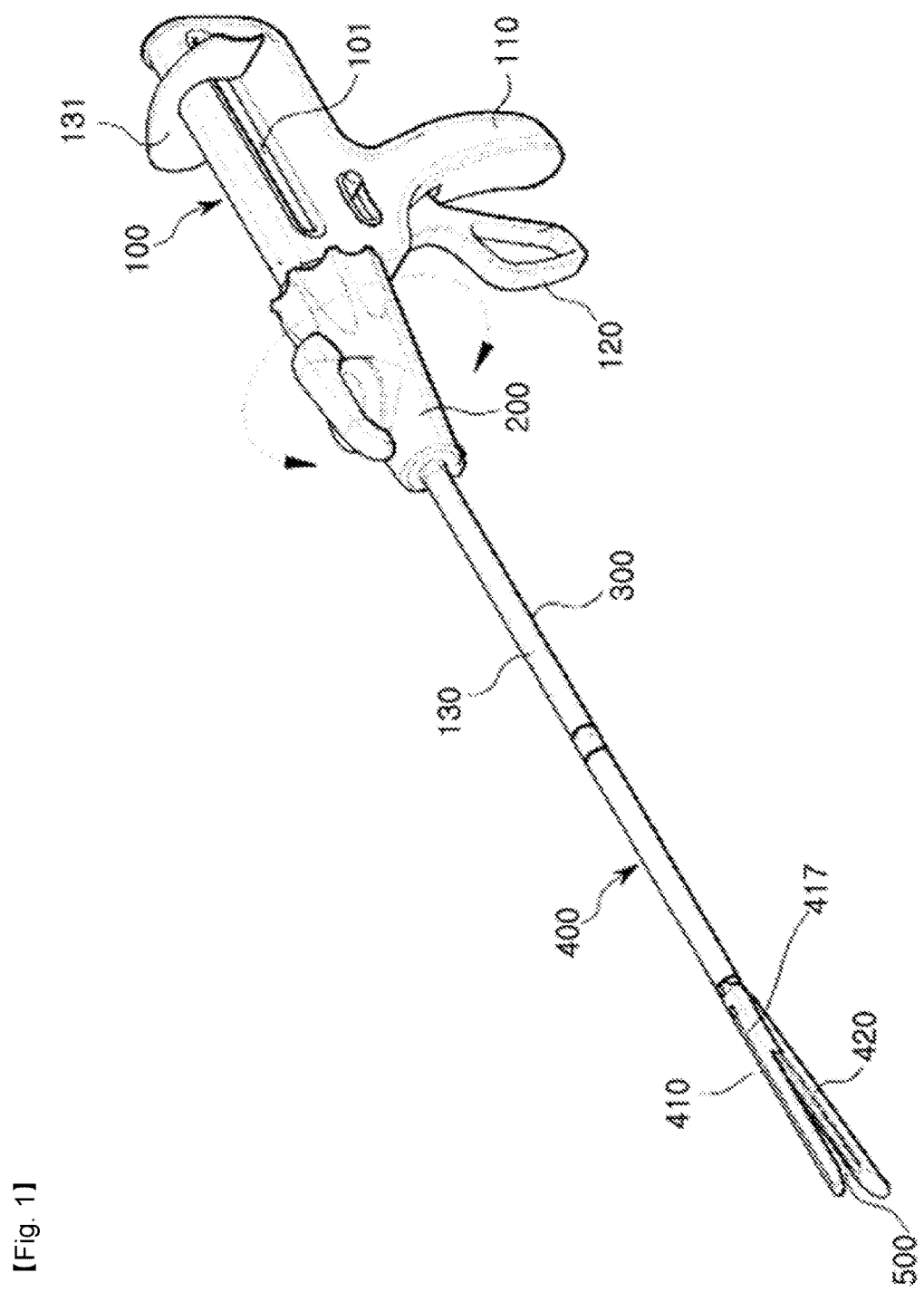
[Fig. 1]

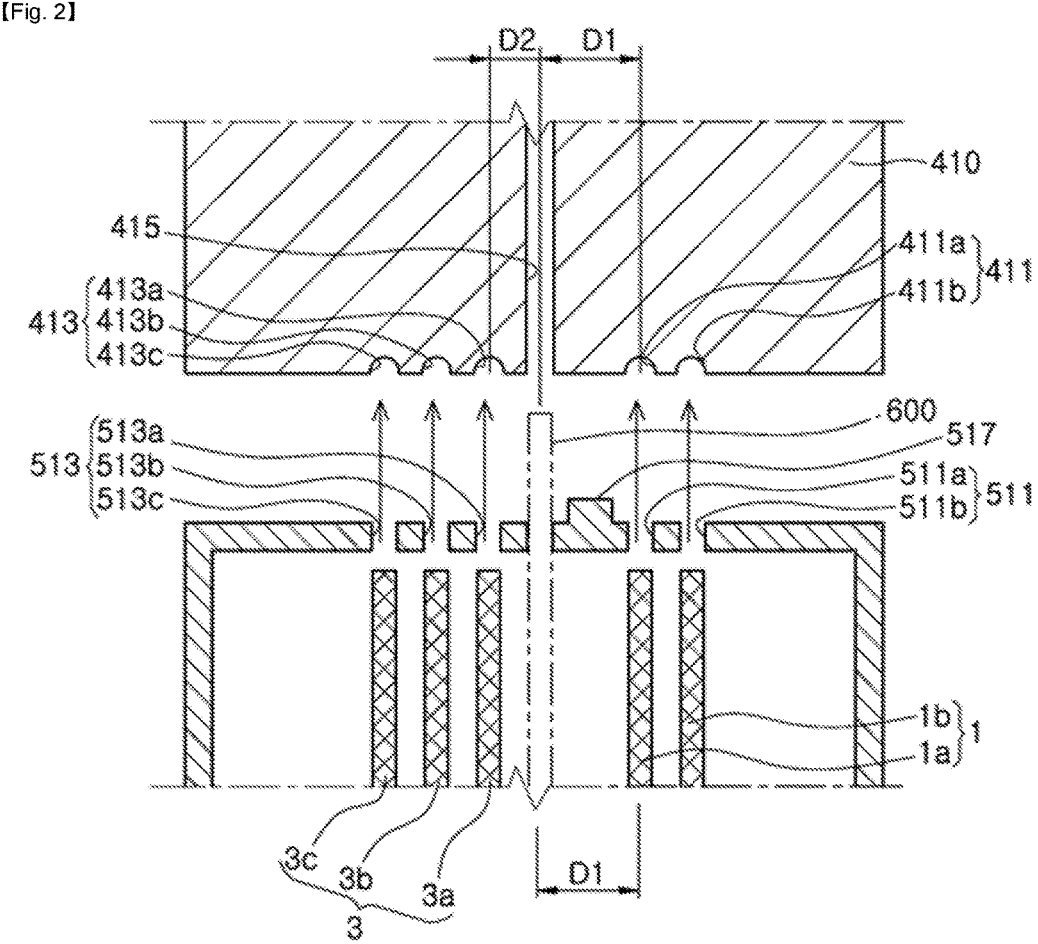
[Fig. 2]

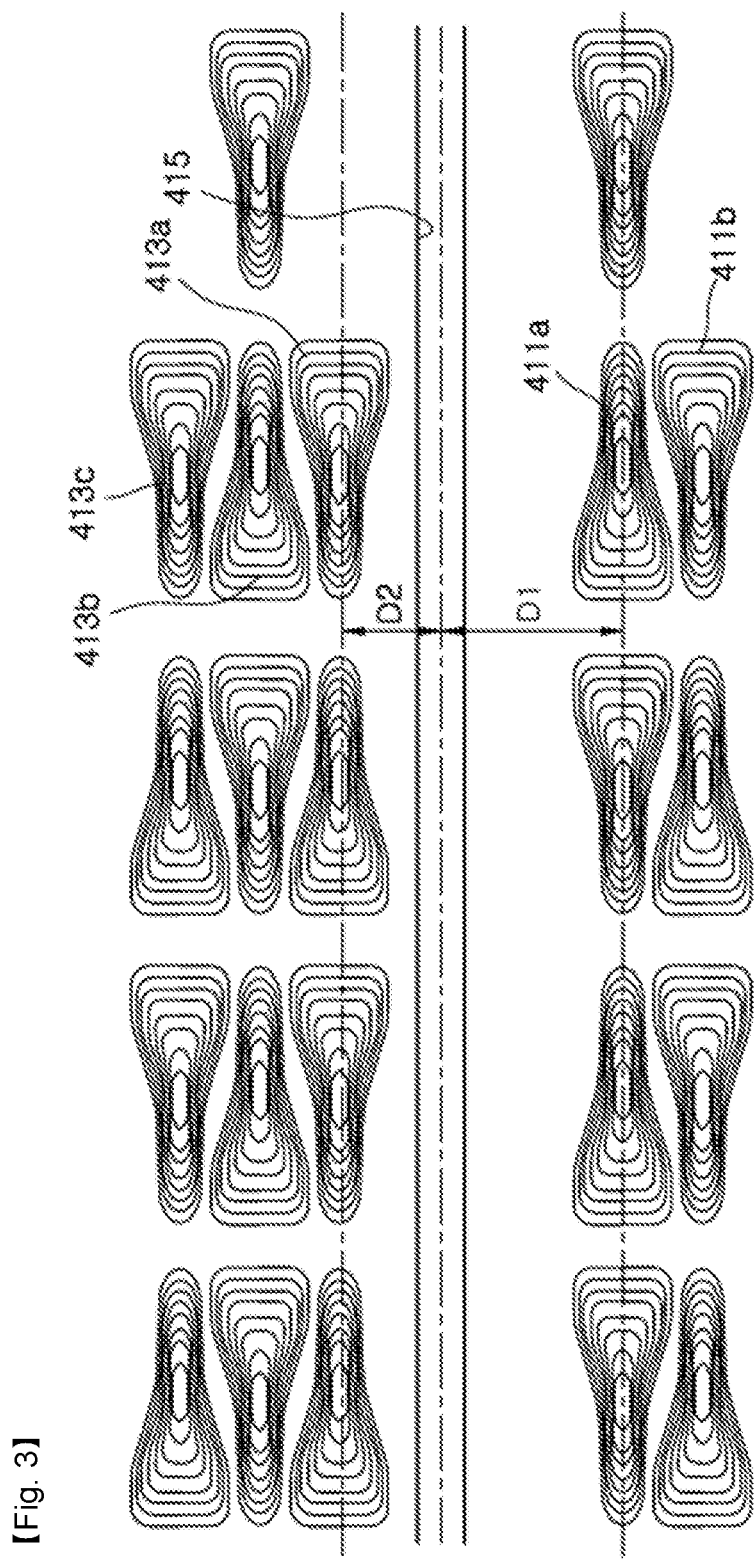
[Fig. 3]

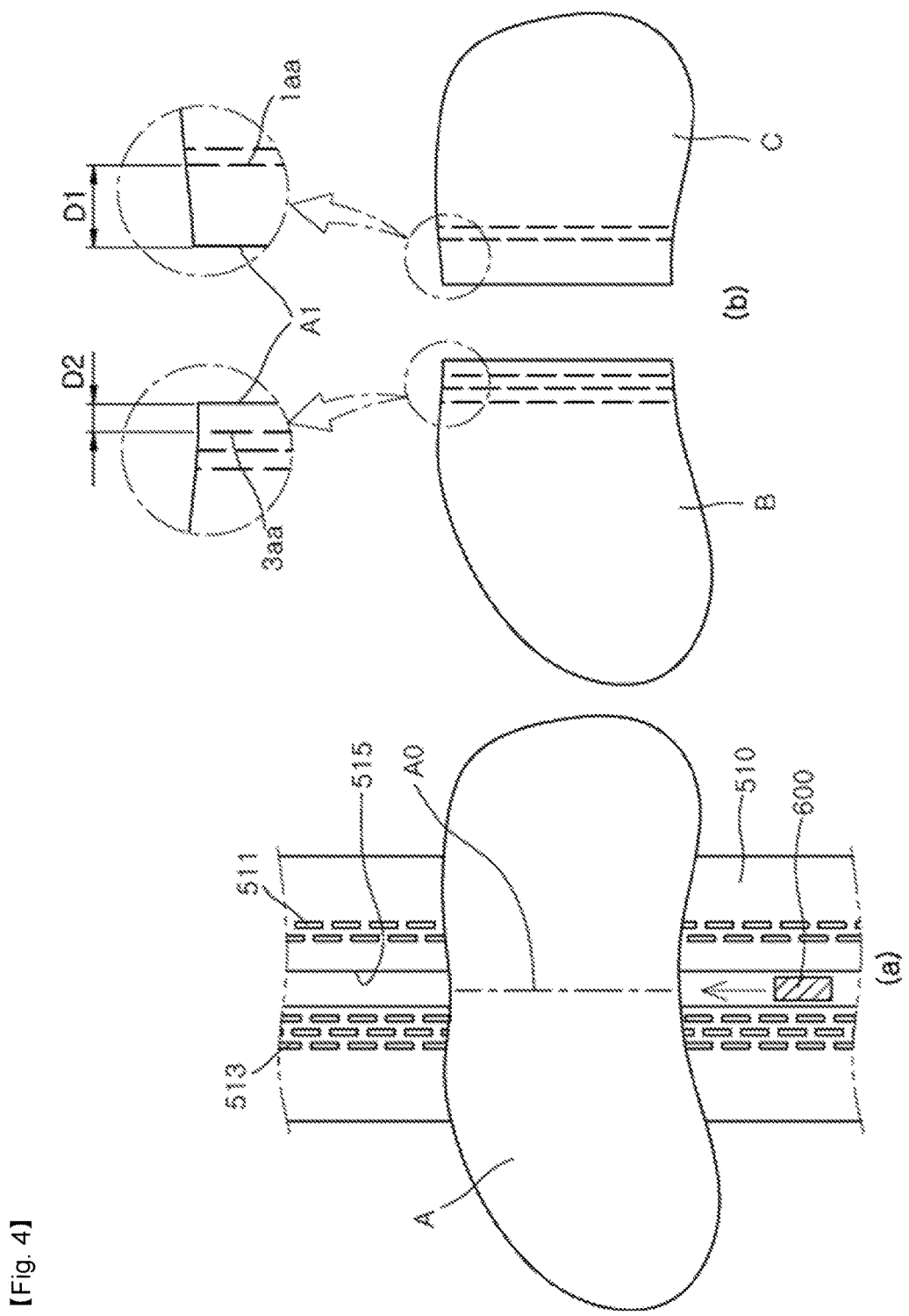
[Fig. 4]

[Fig. 5]
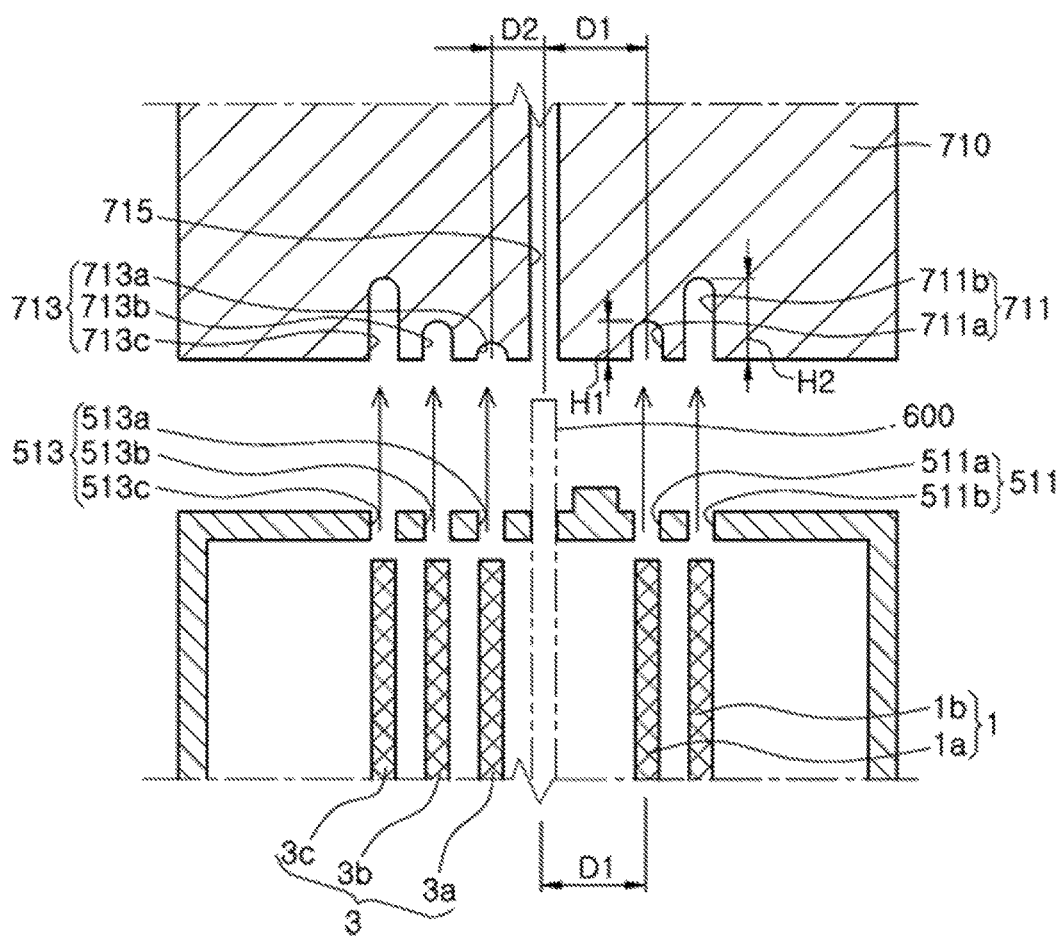

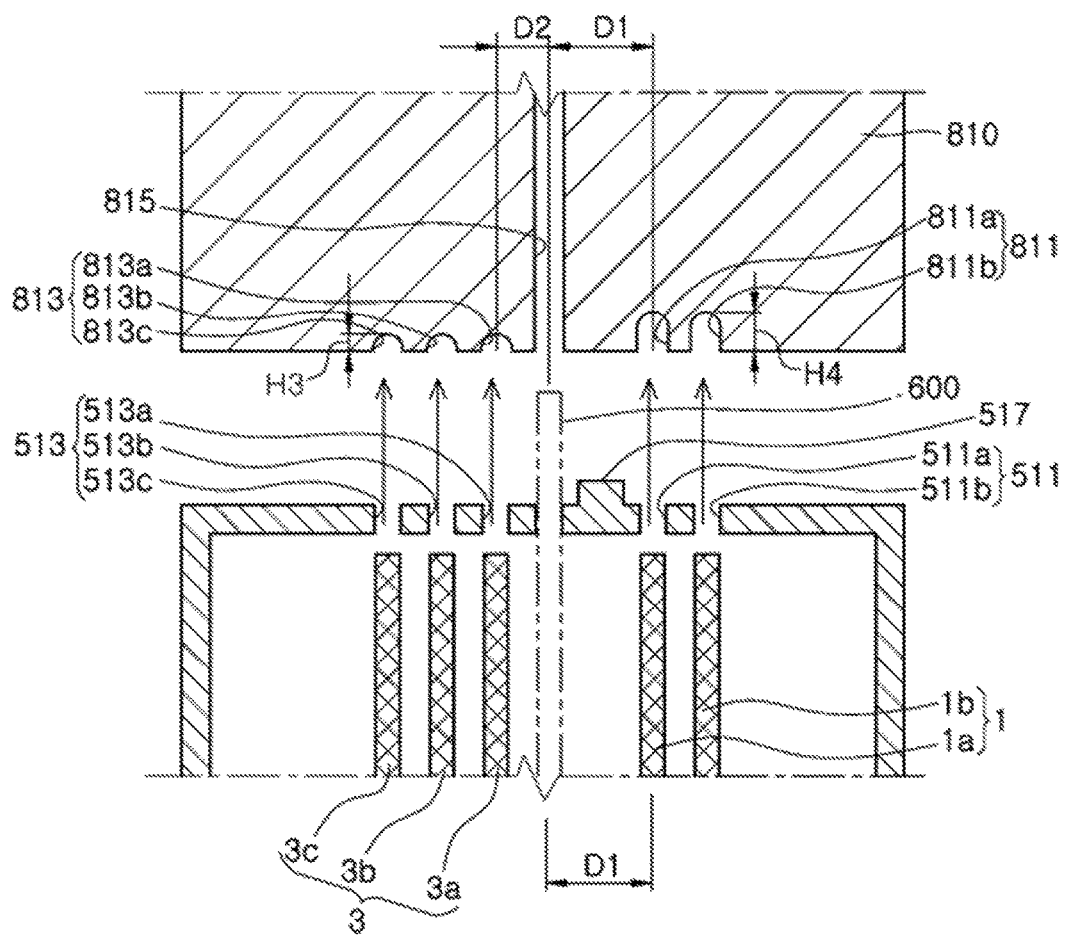
[Fig. 6]

[Fig. 7]
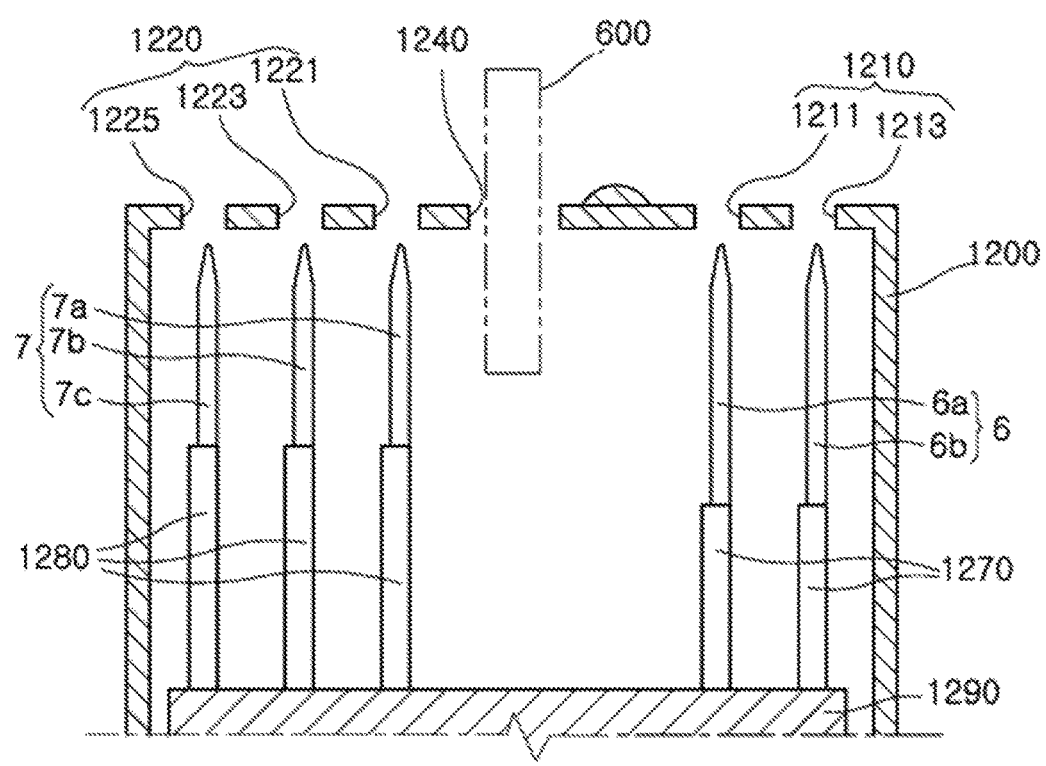

[Fig. 8]
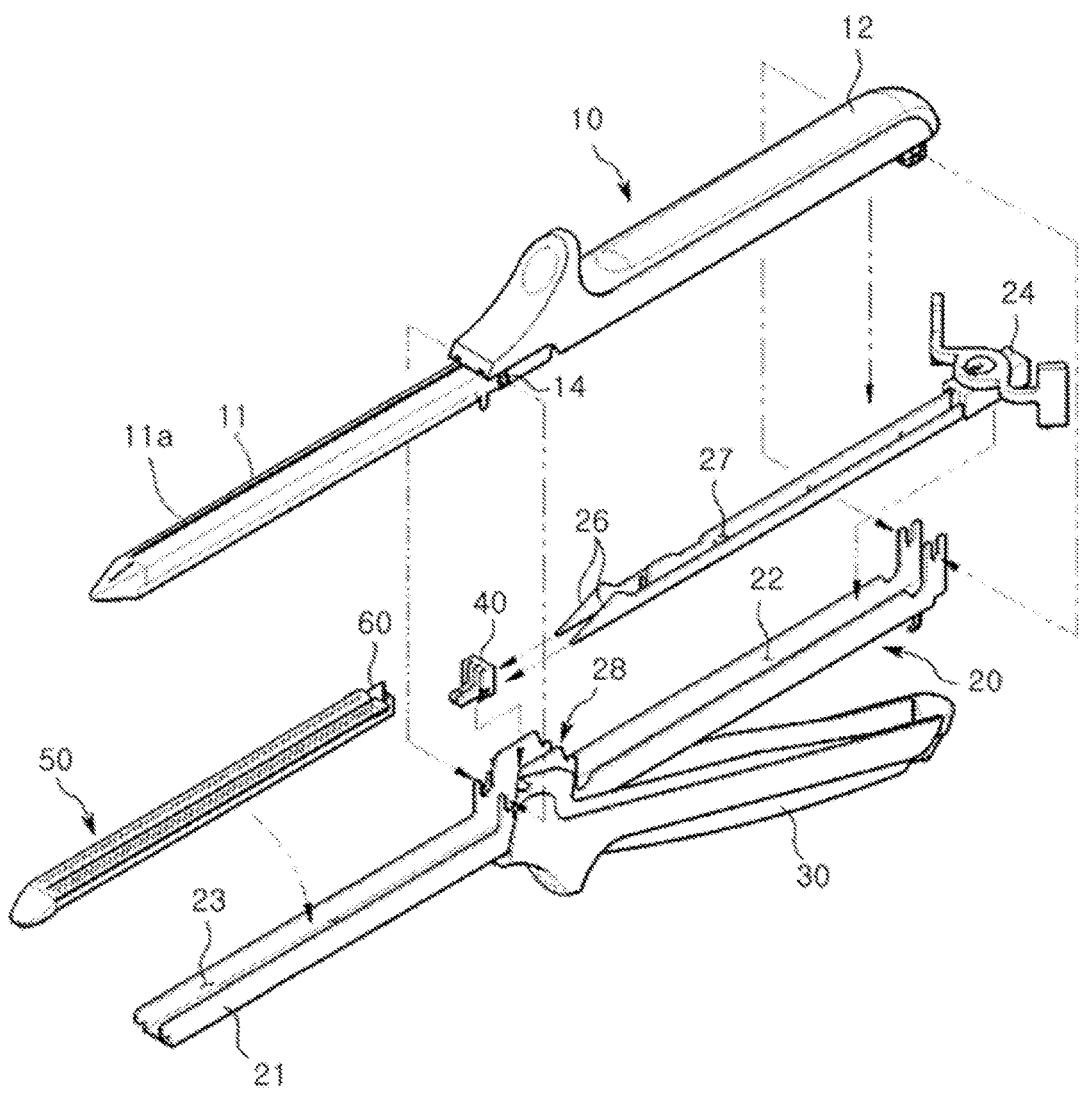

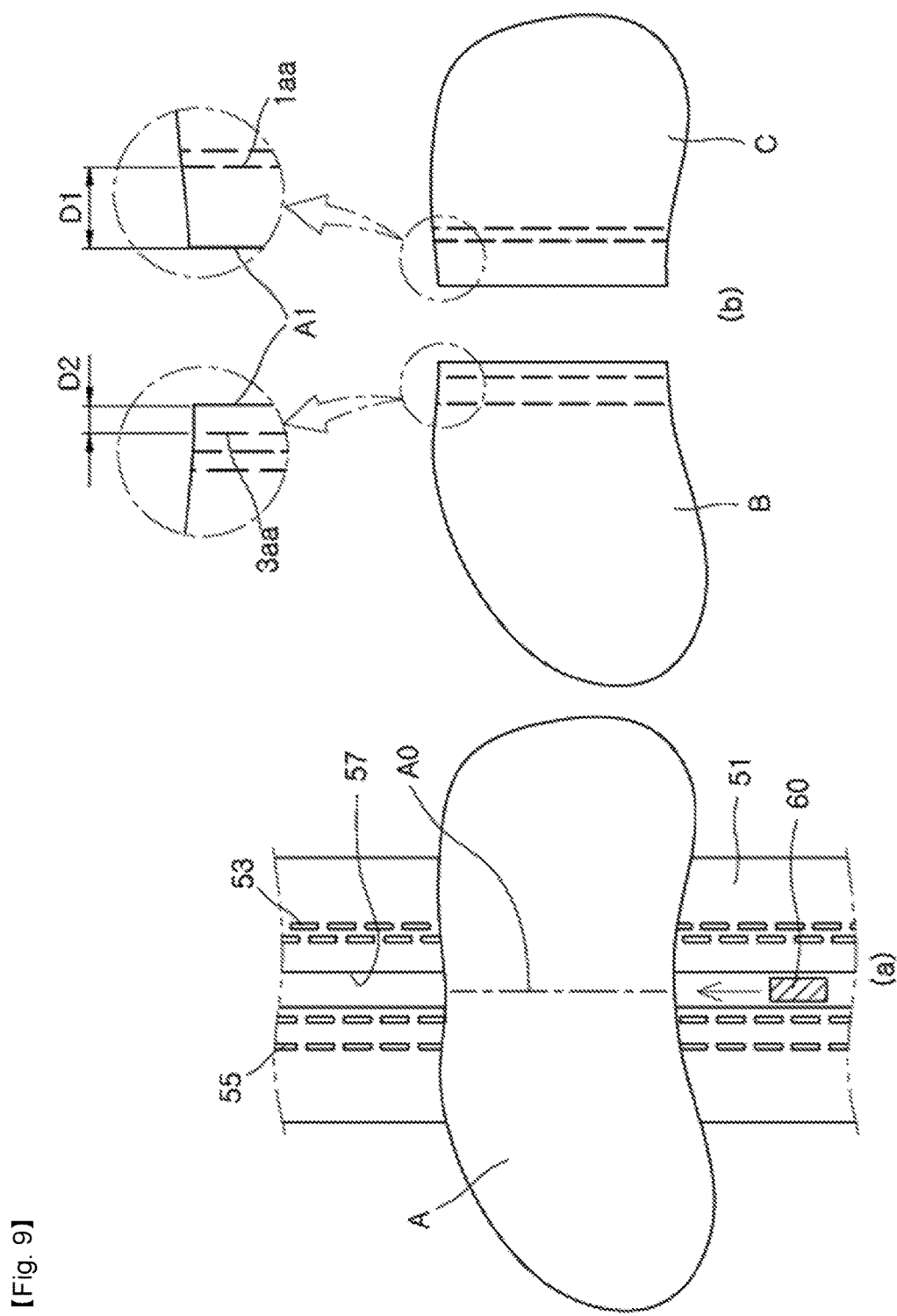

SURGICAL LINEAR STAPLER

CROSS REFERENCE TO PRIOR APPLICATIONS

This application is a National Stage Application of PCT International Patent Application No. PCT/KR2016/002730 filed on Mar. 17, 2016, under 35 U.S.C. § 371, which claims priority to Korean Patent Application Nos. 10-2015-0055272 filed on Apr. 20, 2015 and 10-2015-0174204 filed on Dec. 8, 2015, which are all hereby incorporated by reference in their entirety.

BACKGROUND OF THE INVENTION

(a) Field of the Invention

The present invention relates to a surgical linear stapler, and more particularly to a surgical linear stapler which can stably and conveniently obtain tissue for pathological examination, which is not damaged by a staple, while stapling and cutting a surgical site.

(b) Description of the Related Art

In general, a surgical stapler is a medical instrument mainly used for cutting and anastomosis of an organ in abdominal and thoracic surgery. Such a surgical stapler is classified into an open stapler used in thoracotomy and laparotomy and an endo stapler used in thoracoscopic surgery and celioscopic surgery The surgical stapler has advantages of not only shortening operation time since cutting of a surgical site and anastomosis of an organ are performed at a time, but also accurately stapling the surgical site. Besides, the surgical stapler has advantages of a quicker recovery and a smaller scar than those of when a surgical stitching fiber is used for cutting and stapling tissue, and has been thus widespread in the modern surgical operation. In particular, the surgical stapler has been widely used for cutting cancer tissue and stapling a cut site in cancer surgery.

However, biological tissue adjacent to a section obtained for frozen section tissue examination from a surgical site removed after being stapled and cut by a conventional stapler is damaged by a staple, and it is therefore difficult to correctly examine whether a cancer cell is remained in a cutting margin.

SUMMARY OF THE INVENTION

Accordingly, the present invention is conceived to solve the foregoing problems, and an aspect of the present invention is to provide a surgical linear stapler which can stably and conveniently obtain tissue for pathological examination, which is not damaged by a staple, while stapling and cutting a surgical site.

In accordance with an embodiment of the present invention, there is provided a surgical linear stapler comprising: a staple cartridge which is internally loaded with staples for stapling a surgical site; a cartridge accommodating channel which is formed with a cartridge accommodating groove to accommodate the staple cartridge therein; an anvil which corresponds to the staple cartridge and shapes the staple discharged from the staple cartridge; and a cutter which moves along a lengthwise direction of the staple cartridge by external force and cuts a surgical site arranged in between the staple cartridge and the anvil, wherein the staple cartridge comprises a second cutter guide for guiding the cutter to move along a lengthwise direction of the staple cartridge, and a cartridge body formed with a left staple discharge hole and a right staple discharge hole arranged at opposite sides of the second cutter guide, the right staple discharge hole has a first right staple discharge hole the most adjacent to the second cutter guide in a rightward direction, and the left staple discharge hole has a first left staple discharge hole the most adjacent to the second cutter in a leftward direction, and the first right staple discharge hole is more distant from the second cutter guide than the first left staple discharge hole so as to obtain a tissue area for pathological examination, which is not damaged by the staple, from the surgical site.

In accordance with another embodiment of the present invention, there is provided a surgical linear stapler comprising: a staple cartridge which is internally loaded with staples for stapling a surgical site; a cartridge accommodating channel which is formed with a cartridge accommodating groove to accommodate the staple cartridge therein; an anvil which corresponds to the staple cartridge and shapes the staple discharged from the staple cartridge; and a cutter which is arranged in a back of the staple cartridge and cuts a surgical site arranged in between the staple cartridge and the anvil while moving along a lengthwise direction of the staple cartridge by external force, wherein the anvil comprises a first cutter guide for guiding the cutter to move along a lengthwise direction of the anvil, a right anvil groove having a first right anvil groove the most adjacent to the first cutter guide in a rightward direction with respect to a widthwise direction of the anvil, and a left anvil groove having a first left anvil groove the most adjacent to the first cutter guide in a leftward direction with respect to the widthwise direction of the anvil, and a first distance from a center line of the first right anvil groove to a center line of the first cutter guide is greater than a second distance from a center line of the first left anvil groove to the center line of the first cutter guide so as to obtain a tissue area for pathological examination, which is not damaged by the staple, from a surgical site to be removed in the surgical site.

BRIEF DESCRIPTION OF THE DRAWINGS

FIG. 1 illustrates a surgical linear stapler a first embodiment of according to the present invention;

FIG. 2 illustrates cross-sections of a staple cartridge and an anvil provided in the surgical linear stapler of FIG. 1;

FIG. 3 illustrates contact areas between the anvil of FIG. 2 and skin tissue;

FIG. 4 illustrates that a surgical site is stapled and cut by the surgical linear stapler of FIG. 1;

FIG. 5 illustrates cross-sections of a staple cartridge and an anvil provided in a surgical linear stapler according to a second embodiment of the present invention;

FIG. 6 illustrates cross-sections of a staple cartridge and an anvil provided in a surgical linear stapler according to a third embodiment of the present invention;

FIG. 7 illustrates cross-sections of a staple cartridge and an anvil provided in a surgical linear stapler according to a fourth embodiment of the present invention;

FIG. 8 illustrates a surgical linear stapler according to a fifth embodiment of the present invention; and FIG. 9 illustrates that a surgical site is stapled and cut by a stable cartridge provided in the surgical linear stapler of FIG. 8.

DETAILED DESCRIPTION OF THE EMBODIMENTS

Hereinafter, exemplary embodiments of the present invention for solving the foregoing problems will be described with reference to accompanying drawings. Throughout the following exemplary embodiments, like numerals refer to like elements and repetitive descriptions will be avoided as necessary.

A surgical linear stapler according to a first embodiment of the present invention for obtaining tissue for pathological examination will be described with reference to FIG. 1 to FIG. 4.

Referring to FIG. 1 to FIG. 4, the surgical linear stapler includes a main body 100, a rotary head 200, an extension shaft 300, a stapling shaft 400, a staple cartridge 500 and a cutter 600.

The main body 100 includes a support grip 110 to be gripped by a user, a control grip 120 arranged in front of the support grip 110 and hinge-coupled to the support grip 110, and the stroke bar 130.

The stroke bar 130 is interlocked with the control grip 120 while penetrating the standing extension shaft 300 and the rotary head 200 and also connects with a pull grip 131.

The stroke bar 130 moves forward when the control grip 120 is controlled, and moves backward when a user pulls the pull grip 131 backward.

The pull grip 131 moves in the lengthwise direction of the main body 100 along guide elongated holes 101 formed at left and right sides of the main body 100 in forward and backward longitudinal directions.

The rotary head 200 is provided in the front of the main body 100 and makes the extension shaft 300 and the stapling shaft 400 be rotated 360° while inserting the stroke bar 130 therein.

The extension shaft 300 is placed in between the stapling shaft 400 and the rotary head 200, and a part of the stroke bar 130 is arranged inside the extension shaft 300.

The stapling shaft 400 includes an anvil 410 and a cartridge accommodating channel 420, and the cartridge accommodating channel 420 is formed with a cartridge accommodating groove (not shown) to accommodate the staple cartridge 500 therein.

The staple cartridge 500 is internally filled with staples for stapling the surgical site, and the anvil 410 corresponds to the staple cartridge 500 and shaping the staple discharged from the staple cartridge 500.

The cutter 600 is placed in a back of the staple cartridge 500 and cuts a surgical site between the staple cartridge 500 and the anvil 410 while moving along the lengthwise direction of the staple cartridge 500 by external force.

Detailed structures of the anvil 410 and the staple cartridge 500 are as follows.

The anvil 410 includes a first cutter guide 415 for guiding the cutter 600 to move along the lengthwise direction of the anvil 410, a right anvil groove 411 arranged in a rightward direction of the first cutter guide 415 with respect to the widthwise direction of the anvil 410, and a left anvil groove 413 arranged in a leftward direction of the first cutter guide 415 with respect to the widthwise direction of the anvil 410.

The right anvil groove 411 includes a first right anvil groove 411a which is the most adjacent to the first cutter guide 415 in the rightward direction, and a second right anvil groove 411b which is formed at a right side of the first right anvil groove 411a.

The left anvil groove 413 includes a first left anvil groove 413a which is the most adjacent to the first cutter guide 415 in the leftward direction, a second left anvil groove 413b which is formed at a left side of the first left anvil groove 413a, and a third left anvil groove 413c which is formed at a left side of the second left anvil groove 413b.

In result, the right anvil groove 411 has two rows in the rightward direction of the first cutter guide 415, and the left anvil groove 413 has three rows in the leftward direction of the first cutter guide 415. Of course, the present invention is not limited to the foregoing description. Alternatively, the left anvil groove 413 may have two rows.

To obtain a tissue area for pathological examination, which is not damaged by a staple in a removed surgical site of a surgical site, a first distance D1 from the center line of the first right anvil groove 411a to the center line of the first cutter guide 415 is greater than a second distance D2 from the center line of the first left anvil groove 413a to the center line of the first cutter guide 415.

Further, the first distance D1 is the same as a third distance from the center line of the second left anvil groove 413b to the center line of the first cutter guide 415.

Further, a fourth distance from the center line of the second right anvil groove 411b to the center line of the first cutter guide 415 is the same as a fifth distance from the center line of the third left anvil groove 413c to the center line of the first cutter guide 415. Here, the left anvil groove 413 and the right anvil groove 411 have the same depth.

Of course, the present invention is not limited to the foregoing description. As necessary, the first distance and the third distance may be different from each other, and the fourth distance and the fifth distance may be also different from each other.

In addition, an indicator 417 for indicating a right position of the surgical linear stapler is provided on an outer surface of the anvil 410.

Specifically, the indicator 417 indicates the position of the right anvil groove 411 so that the tissue area for pathological examination can be included in a surgical site, i.e. a first surgical site C.

The indicator 417 may be attached to the anvil 410 in the form of a colored tape distinctive from a view of the exterior, or a projection having a certain shape. Alternatively, the indicator 417 may be made of a material with a fluorescent substance, or a lighting unit such as a light emitting diode. Further, the present invention is not limited to the foregoing description, and the indicator 417 may be placed on at least one of an outer surface of the anvil 410 and an outer surface of the cartridge accommodating channel 420.

In result, the indicator 417 indicates a position of a right staple discharge hole 511 so that the tissue area for pathological examination can be included in a surgical site of an organ from which is removed, thereby preventing a mistake in surgery.

Further, the staple cartridge 500 includes a cartridge body 510 which is formed with a second cutter guide 515 for guiding the cutter 600 to move along the lengthwise direction of the staple cartridge 500, the right staple discharge hole 511 corresponding to the right anvil groove 411, and a left staple discharge hole 513 corresponding to the left anvil groove 413.

The second cutter guide 515 is provided as a hole in a center portion of the cartridge body 510. Of course, the present invention is not limited to the foregoing description, and the second cutter guide 515 may be formed at a position deviated from the center of the cartridge body 510 in the widthwise direction.

The right staple discharge hole 511 includes a first right staple discharge hole 511a the most adjacent to the second cutter guide 515 in the rightward direction, and a second right staple discharge hole 511b formed at a right side of the first right staple discharge hole 511a.

The first right staple discharge hole 511a corresponds to the first right anvil groove 411a, and the second right staple discharge hole 511b corresponds to the second right anvil groove 411b. The first right staple discharge hole 511a is loaded with a first right staple 1a, and the second right staple discharge hole 511b is loaded with a second right staple 1b.

The left staple discharge hole 513 includes a first left staple discharge hole 513a the most adjacent to the second cutter guide 515 in the leftward direction, a second left staple discharge hole 513b formed at a left side of the first left staple discharge hole 513a, and a third left staple discharge hole 513c formed at a left side of the second left staple discharge hole 513b.

The first left staple discharge hole 513a corresponds to the first left anvil groove 413a, the second left staple discharge hole 513b corresponds to the second left anvil groove 413b, and the third left staple discharge hole 513c corresponds to the third left anvil groove 413c.

Here, the first left staple discharge hole 513a is loaded with a first left staple 3a, the second left staple discharge hole 513b is loaded with a second left staple 3b, and the third left staple discharge hole 513c is loaded with a third left staple 3c.

According to an embodiment of the present invention, there are no limits to the number of rows corresponding to the staple discharge holes. However, it is preferable that the number of rows corresponding to the left staple discharge holes 513 is more than the number of rows corresponding to the right staple discharge holes 511.

The reasons are as follows. A surgical site stapled by left staples 3 discharged from the left staple discharge hole 513 has to be stitched up densely since it is remained in a human body, whereas there are no needs to densely stitch up a surgical site stapled by right staples 1 discharged from the right staple discharge hole 511 since it is removed.

The first right staple discharge hole 511a is more distant from the second cutter guide 515 than the first left staple discharge hole 513a in order to obtain a tissue area for pathological examination, which is not damaged by the staple, from the surgical site.

On the top surface the cartridge body 510, a protrusion 517 protrudes between the second cutter guide 515 and the first right staple discharge hole 511a.

The protrusion 517 presses and holds an area near a cutting section when the cutter 600 cuts a surgical site in the state that the surgical site is clamped by the anvil 410 and the staple cartridge 500, thereby making the surgical site be stably cut.

The protrusion 517 minimizes a gap between the anvil 410 and the staple cartridge 500 when the surgical site is clamped by the anvil 410 and the staple cartridge 500.

The protrusion 517 may protrude as a straight line along the lengthwise direction of the cartridge body while having an arc-shaped cross section, or may protrude with embossing patterns at regular intervals.

Of course, the present invention is not limited to the foregoing description, and the protrusion 517 may be omitted.

As shown in (a) of FIG. 4, a surgical site A arranged above the staple cartridge 500 is cut by the cutter 600 into two surgical sites with respect to a virtual cutting line A0. One of the two surgical sites is a first surgical site C to be removed, and the other one is a second surgical site B to be remained in a human body.

Referring to (b) of FIG. 4, the first surgical site C has stapling lines of two rows parallel with a cutting section A1, and the second surgical site B has stapling lines of three rows parallel with the cutting section A1.

Here, the distance D1 between a first right stapling line 1aa, which is near to the cutting section A1, of the stapling lines in the first surgical site C and the cutting section A1 is greater than the distance D2 between a first left stapling line 3aa, which is near to the cutting section A1, of the stapling lines in the second surgical site B and the cutting section A1.

Biological tissue placed in between the cutting section A1 and the first right stapling line 1aa in the first surgical site C is suitable for the tissue for pathological examination since it is not damaged at all.

The distance D1 between the cutting section A1 and the first right stapling line 1aa is possible as long as it is to obtain tissue for pathological examination. However, it is preferable that the distance is substantially equal to the distance between the cutting section A1 and the second right stapling line among the stapling lines formed in the second surgical site B.

The reasons are because the surgical site A is more stably cut if the surgical site A is held by the staples at corresponding opposite sides of the second cutter guide 515, i.e., at the same distances from the cutting section to the opposite stapling lines when the surgical site A is cut by the cutter 600.

In result, the distance from the cutting section to the stapling line of an organ site to be removed while cutting one organ into two areas and stapling them is set to be greater than the distance from the cutting section to the stapling line of the surgical site to be remained in a human body, thereby preventing a cutting margin of biological tissue for examination from being damaged in the surgical site to be removed. Therefore, it is possible to stably and conveniently obtain a tissue area for pathological examination, which is not damaged by a staple, in a surgical site of an organ to be removed.

Below, cross-sections of the staple cartridge and the anvil provided in the surgical linear stapler according to a second embodiment of the present invention will be described with reference to FIG. 5.

The elements of the surgical linear stapler in the second embodiment are similar to those of the surgical stapler according to the first embodiment. However, an anvil 710 provided in the surgical linear stapler according to the second embodiment is different from the anvil provided in the surgical linear stapler according to the first embodiment.

Specifically, the anvil 710 is formed with a first cutter guide 715, a right anvil groove 711, a left anvil groove 713 arranged in the leftward direction, in which the right anvil groove 711 includes a first right anvil groove 711a and a second right anvil groove 711b, and the left anvil groove 713 includes a first left anvil groove 713a, a second left anvil groove 713b and a third left anvil groove 713c.

To more firmly hold an area, which is near to the first cutter guide 715 and stapled by a stapler, of a surgical site to be removed in a surgical site, a depth H1 of the first right anvil groove is shallower than a depth H2 of the second right anvil groove.

That is, the height of the staple on the first right stapling line after shaping the first right staple 1a corresponding to the first right anvil groove 711a is lower than the height of the stable on the second right stapling line after shaping the second right staple 1b corresponding to the second right anvil groove 711b, thereby more tightly holding the corresponding skin tissue.

As the corresponding skin tissue is more tightly held on the first right stapling line, content of the surgical site, e.g. blood and the like are prevented from leakage.

Likewise, to more firmly hold an area, which is near to the first cutter guide 715 and stapled, in a remained surgical site of the surgical site, the depth of the first left anvil groove 713a is shallower than the depth of the second left anvil groove 713b, and the depth of the second left anvil groove 713b is shallower than the depth of the third left anvil groove 713c.

In the remained surgical site, the height of the staple on the first left stapling line after shaping the first left staple 3a corresponding to the first left anvil groove 713a is made as low as possible to thereby prevent the content of the remained surgical site from leakage, and the height of the staple on the third left stapling line after shaping the third left staple 3c corresponding to the third left anvil groove 713c is made as high as possible to thereby decrease pressure applied to the content of the remained surgical site.

Below, cross-sections of the staple cartridge and the anvil provided in the surgical linear stapler according to a third embodiment of the present invention will be described with reference to FIG. 6.

The elements of the surgical linear stapler in the third embodiment are similar to those of the surgical stapler according to the first embodiment. However, an anvil 810 provided in the surgical linear stapler according to the third embodiment is different from the anvil provided in the surgical linear stapler according to the first embodiment.

Specifically, the anvil 810 is formed with a first cutter guide 815, a right anvil groove 811, and a left anvil groove 813 arranged in the leftward direction, in which the right anvil groove 811 includes a first right anvil groove 811a and a second right anvil groove 811b, and the left anvil groove 813 includes a first left anvil groove 813a, a second left anvil groove 813b and a third left anvil groove 813c.

To make the height of the stapling area of the surgical site to be remained in the surgical site be lower than the height of the stapling area of the surgical site to be removed, a first depth H3 of the left anvil groove is shallower than a second depth H4 of the right anvil groove.

Here, both the first right anvil groove 811a and the second right anvil groove 811b have the same second depth H4, and all the first left anvil groove 813a, the second left anvil groove 813b and the third left anvil groove 813c have the same first depth H3.

This is to more safely prevent content from leakage since the remained surgical site is leaved in a human body.

Below, cross-sections of the staple cartridge and the anvil provided in the surgical linear stapler according to a fourth embodiment of the present invention will be described with reference to FIG. 7.

The elements of the surgical linear stapler in the fourth embodiment are similar to those of the surgical stapler according to the first embodiment. However, a staple cartridge provided in the surgical linear stapler according to the fourth embodiment is different from the staple cartridge provided in the surgical linear stapler according to the first embodiment.

The staple cartridge includes a cartridge body 1200, which is formed with a second cutter guide 1240, a right staple discharge hole 1210 and a left staple discharge hole 1220; a left pressing member 1280; a right pressing member 1270; and a driving wedge 1290.

The right staple discharge hole 1210 includes a first right staple discharge hole 1211 and a second right staple discharge hole 1213; and the left staple discharge hole 1220 includes the first left staple discharge hole 1221, the second left staple discharge hole 1223 and a third left staple discharge hole 1225.

The right staple discharge hole 1210 is loaded with a right staple 6, and the left staple discharge hole 1220 is loaded with the left staple 7. The right staple 6 is shaped by the right anvil groove (not shown), and the left staple 7 is shaped by the left anvil groove (not shown).

The first right staple discharge hole 1211 is loaded with a first right staple 6a, and the second right staple discharge hole 1213 is loaded with a second right staple 6b.

The first left staple discharge hole 1221 is loaded with a first left staple 7a, the second left staple discharge hole 1223 is loaded with a second left staple 7b, and the third left staple discharge hole 1225 is loaded with a third left staple 7c.

Here, the leg of the right staple 6 to be shaped by the right anvil groove is different in length from the leg of the left staple 7 to be shaped by the left anvil groove. That is, the leg of the right staple 6 is longer than the leg of the left staple 7.

If distances between the staple discharge holes to the anvil grooves are uniform, the height of the staple after shaping becomes higher as the leg of the staple increases.

In result, the leg of the right staple to be shaped by the right anvil groove is longer than the leg of the left staple to be shaped by the left anvil groove, so that tissue of a surgical site to be cut and removed can be more loosely held, thereby minimizing the damage of the tissue area for pathological examination.

By the way, the right pressing member 1270 presses the right staple 6 toward the outside of the right staple discharge hole 1210 in order to discharge the right staple 6, and the left pressing member 1280 presses the left staple 7 toward the outside of the left staple discharge hole 1220 in order to discharge the left staple 7.

Since the leg of the right staple 6 is longer than the leg of the left staple 7, the length of the right pressing member 1270 is shorter than the length of the left pressing member 1280.

Of course, the present invention is not limited to the foregoing description. Alternatively, the right pressing member 1270 and the left pressing member 1280 may be different in length from each other regardless of the leg length of the staple.

The driving wedge 1290 pushes up both the right pressing member 1270 and the left pressing member 1280 toward the right staple discharge hole 1210 and the left staple discharge hole 1220, respectively. Thus, the right staple 6 and the left staple 7 are discharged from the right staple discharge hole 1210 and the left staple discharge hole 1220, respectively.

Below, a surgical linear stapler according to a fifth embodiment of the present invent ion will be described with reference to FIG. 8 and FIG. 9.

The surgical linear stapler according to the fifth embodiment includes an upper body 10, a lower body 20, a lower grip 30, a staple cartridge 50 and a cutter 60.

Specifically, the upper body 10 includes an anvil 11, a upper grip 12 arranged in a back of the anvil 11, and a coupling projection 14 arranged in a region where the upper grip 12 and the anvil 11 are connected.

In addition, an indicator 11a for indicating a right position of the surgical linear stapler is provided on an outer surface of the anvil 11.

The lower body 20 includes a cartridge accommodating channel 21, a guide slot 22 arranged in a back of the cartridge accommodating channel 21, and a coupling portion 28 arranged in a region where the cartridge accommodating channel 21 and the guide slot 22 are connected.

Further, the cartridge accommodating channel 21 is formed with a cartridge accommodating groove 23 in which the staple cartridge 50 is accommodated.

The guide slot 22 is provided with a sliding member 24 that moves along the lengthwise direction of the guide slot 22. The sliding member 24 includes a driving wedge 26 for discharging the staple loaded in the staple cartridge 50, and a push bar 27 for moving the cutter 60.

The coupling portion 28 is provided with a stopper 40 for restricting the movement of the sliding member 24, and the stopper 40 is formed with a plurality of through holes through which the driving wedge 26 and the push bar 27 pass.

Further, the coupling portion 28 receives the coupling projection 14 so that the upper body 10 and the lower body 20 can be coupled with each other.

The lower grip 30 is placed beneath the lower body 20 and hinge-coupled to the coupling portion 28.

The staple cartridge 50 is internally loaded with staples for stapling the surgical site, and the cutter 60 is placed in the back of the staple cartridge 50.

The cutter 60 cuts a surgical site between the staple cartridge 50 and the anvil 11 while moving along the lengthwise direction of the staple cartridge 50 by external force.

The staple cartridge 50 includes a second cutter guide 57 for guiding the cutter 60 to move along the lengthwise direction of the staple cartridge 50, and a cartridge body 51 formed with left staple discharge holes 55 and right staple discharge holes 53 arranged at opposite sides of the second cutter guide 57.

Each of the left staple discharge holes 55 and the right staple discharge holes 53 has two rows at each side of the second cutter guide 57 on the contrary to those of the foregoing embodiments.

Further, the rows of the left staple discharge holes 55 are spaced differently from the rows of the right staple discharge holes 53. Specifically, the rows of the right staple discharge holes 53 are formed more narrowly than the rows of the left staple discharge holes 55.

Further, the first row of the right staple discharge hole 53 is more distant from the second cutter guide 57 than the first row of the left staple discharge hole 55 in order to obtain tissue area for pathological examination, which is not damaged by the staples, of the surgical site.

Specifically, as shown in (a) of FIG. 9, the surgical site A arranged above the staple cartridge 50 is cut by the cutter 60 into two surgical sites with respect to a virtual cutting line A0. One of the two surgical sites is a first surgical site C, and the other one is a second surgical site B to be remained in a human body.

Referring to (b) of FIG. 9, the first surgical site C has stapling lines of two rows parallel with a cutting section A1, and the second surgical site B has stapling lines of two rows parallel with the cutting section A1.

Here, the distance D1 between a first right stapling line 1aa, which is near to the cutting section A1, of the stapling lines in the first surgical site C and the cutting section A1 is greater than the distance D2 between a first left stapling line 3aa, which is near to the cutting section A1, of the stapling lines in the second surgical site B and the cutting section A1.

Biological tissue placed in between the cutting section A1 and the first right stapling line 1aa in the first surgical site C is suitable for the tissue for pathological examination since it is not damaged at all.

Here, if both the second row of the right staple discharge hole 53 and the second row of and the left staple discharge hole 55 are at the same distance from the second cutter guide 57, it is possible to obtain a larger tissue area for pathological examination as a space between the rows of the right staple discharge holes 53 gets narrower.

Of course, the present invention is not limited to the foregoing description. Alternatively, the structures of the staple cartridge and the anvil may be substantially the same as those of the surgical linear stapler according to the first to fourth embodiments.

The surgical linear stapler according to the present invention has effects as follows.

First, the first right staple discharge hole and the first left staple discharge hole arranged at opposite sides with respect to the second cutter guide are different in distance from the second cutter guide from each other, so that the distance from the cutting section to the stapling line of an organ to be removed is greater than the distance from the cutting section to the stapling line of the surgical site to be remained in a human body while cutting one organ into two areas and stapling them, thereby having an advantage of preventing the cutting margin of the biological tissue for the examination from being damaged within the tissue of the organ to be removed.

Second, the first right anvil groove and the first left anvil groove arranged at opposite sides with respect to the first cutter guide are different in distance from the first cutter guide from each other, so that the distance from the cutting section to the stapling line of an organ to be removed is greater than the distance from the cutting section to the stapling line of the surgical site to be remained in a human body while cutting one organ into two areas and stapling them, thereby having an advantage of preventing the cutting margin of the biological tissue for the examination from being damaged within the tissue of the organ to be removed. In result, it is possible to stably and conveniently obtain a tissue area for pathological examination, which is not damaged by a staple, in tissue of an organ to be removed.

Third, the protrusion is arranged on the top of the cartridge body between the first right staple discharge hole and the second cutter guide, so that the protrusion can press and hold an area near the cutting section when the cutter cuts a surgical site in the state that the surgical site is clamped by the anvil and the staple cartridge, thereby making the surgical site be stably cut.

Fourth, the depth of the first right anvil groove is shallower than the depth of the second right anvil groove in order to more firmly hold an area, which is near to the first cutter guide and stitched up by a staple, of a surgical site to be removed in the surgical site, so that corresponding skin tissue is more tightly held on the first right stapling line thereby having an advantage of preventing content of the surgical site, e.g. blood and the like from leakage.

Fifth, the leg of the right staple shaped by the right anvil groove is longer than the leg of the left staple shaped by the left anvil groove, so that tissue of a surgical site to be cut and removed can be more loosely held, thereby minimizing the damage of the tissue area for pathological examination.

Sixth, the indicator for indicating the position of the right staple discharge hole is placed on at least one of the outer surface of the anvil and the outer surface of the cartridge accommodating channel, and thus a tissue area for pathological examination is included in a surgical site of an organ which is removed, thereby preventing a mistake in surgery.

As described above, a surgical stapler according to the present invention can stably and conveniently obtain a tissue area for pathological examination, which is not damaged by a staple, within a tissue of an organ to be removed, and be therefore widely used as a surgical stapler for cutting and anastomosis of an organ in abdominal and thoracic surgery of cutting cancer tissue and stapling the cutting site.

Although a few exemplary embodiments of the present invention have been shown and described, it will be appreciated by those skilled in the art that changes may be made in these embodiments without departing from the principles and spirit of the invention, the scope of which is defined in the appended claims and their equivalents.

What is claimed is:

1. A surgical linear stapler comprising:
a staple cartridge configured to be internally loaded with staples for stapling a surgical site;
a cartridge accommodating channel formed with a cartridge accommodating groove to accommodate the staple cartridge therein;
an anvil configured to form the staples discharged from the staple cartridge;
a cutter configured to move along a lengthwise direction of the staple cartridge by external force and to cut the surgical site arranged in between the staple cartridge and the anvil;
a pressing member configured to press and discharge the staples toward the outside of the staple cartridge;
wherein the staple cartridge comprises a cutter guide for guiding the cutter to move along the lengthwise direction of the staple cartridge, and a cartridge body formed with one or more rows of left staple discharge holes and one or more rows of right staple discharge holes arranged at opposite sides of the cutter guide, and
wherein the one or more rows of left staple discharge holes and the one or more rows of right staple discharge holes are asymmetrically arranged with respect to the cutter guide; and
an indicator configured to indicate a position of the one or more rows of right staple discharge holes and arranged at a right side of the cutter guide for indicating an asymmetry of the surgical linear stapler so that an object tissue for pathological examination is included in a first surgical site to be removed by the cutter; further comprising a plurality of members arranged at a predetermined interval along the lengthwise direction of the staple cartridge between the cutter guide and a first row of right staple discharge holes the most adjacent to the cutter guide in a rightward direction, and configured to press and hold a tissue area near the cutting section when the surgical site is cut.

2. The surgical linear stapler according to claim 1, wherein the indicator configured to be arranged in at least one of an outer surface of the anvil and an outer surface of the cartridge accommodating channel.

3. A surgical linear stapler comprising:
a staple cartridge configured to be internally loaded with staples for stapling a surgical site;
a cartridge accommodating channel formed with a cartridge accommodating groove to accommodate the staple cartridge therein;
an anvil configured to form the staples discharged from the staple cartridge;
a cutter configured to cut the surgical site arranged in between the staple cartridge and the anvil while moving along a lengthwise direction of the staple cartridge by external force;
a pressing member configured to press and discharge the staples toward the outside of the staple cartridge;
wherein the anvil comprises a first cutter guide for guiding the cutter to move along a lengthwise direction of the anvil, one or more rows of right anvil grooves arranged at one side of the first cutter guide, and one or more rows of left anvil grooves arranged at the other side of the first cutter guide, and
wherein the one or more rows of left anvil grooves and the one or more rows of right anvil grooves are asymmetrically arranged with respect to the first cutter guide; and
an indicator configured to indicate a position of the one or more rows of right anvil grooves and arranged at a right side of the first cutter guide for indicating an asymmetry of the surgical linear stapler so that an object tissue for pathological examination is included in a first surgical site to be removed by the cutter; further comprising a plurality of members arranged at a predetermined interval along the lengthwise direction of the staple cartridge between the cutter guide and a first row of right staple discharge holes the most adjacent to the cutter guide in a rightward direction, and configured to press and hold a tissue area near the cutting section when the surgical site is cut.

4. The surgical linear stapler according to claim 3, wherein the one or more rows of right anvil grooves comprises a first row of right anvil grooves the most adjacent to the first cutter guide in a rightward direction and a second row of right anvil grooves formed at a right side of the first row of right anvil grooves, and
wherein a distance from a center line of the first row of right anvil grooves to a center line of the first cutter guide is greater than another distance from the center line of the first row of right anvil grooves to a center line of the second row of right anvil grooves.

5. The surgical linear stapler according to claim 4, wherein a groove depth of the first row of right anvil grooves is shallower than a groove depth of the second row of right anvil grooves so as to more firmly hold a tissue area near to the first cutter guide within an area to be stapled by the staple in the first surgical site.

6. The surgical linear stapler according to claim 4, wherein a groove depth of the one of more rows of left anvil grooves is shallower than a groove depth of the one of more rows of right anvil grooves so as to make a height of a stapling area of a second surgical site to be remained in a human body be lower than a height of a stapling area of a first surgical site to be removed by the cutter.

7. The surgical linear stapler according to claim 3, wherein a leg of a right staple formed by a right anvil groove of the one or more rows of right anvil grooves and a leg of a left staple formed by a left anvil groove of the one or more rows of left anvil grooves are different in length from each other.

8. The surgical linear stapler according to claim 1,
wherein the staples comprises right staples loaded within the one or more rows of right staple discharge holes and left staples loaded within the one or more rows of left staple discharge holes,
wherein the pressing member comprises right pressing members configured to press and discharge the right staples toward the outside of the one or more rows of right staple discharge holes and left pressing members configured to press and discharge the left staples toward the outside of the one or more rows of left staple discharge holes, and the right pressing members and the left pressing members are asymmetrically arranged with respect to the cutter guide, and wherein the surgical linear stapler further comprises a driving wedge pushes up the right pressing members and the left pressing members toward the one or more rows of right staple discharge holes and the one or more rows of left staple discharge holes, respectively.

9. A surgical linear stapler comprising:
a staple cartridge configured to be internally loaded with staples for stapling a surgical site
a cartridge accommodating channel formed with a cartridge accommodating groove to accommodate the staple cartridge therein;
an anvil configured to form the staples discharged from the staple cartridge;
a cutter configured to move along a lengthwise direction of the staple cartridge by external force and to cut the surgical site arranged in between the staple cartridge and the anvil;
a pressing member configured to press and discharge the staples toward the outside of the staple cartridge;
wherein the staple cartridge comprises a cutter guide for guiding the cutter to move along a lengthwise direction of the staple cartridge, and a cartridge body formed with one or more rows of left staple discharge holes and one or more rows of right staple discharge holes arranged at opposite sides of the cutter guide,
wherein the surgical site comprises a first surgical site to be removed by the cutter and a second surgical site to be remained in a human body,
wherein a first right stapling line stapled by a first row of right staples is formed on the first surgical site, and a first left stapling line stapled by a first row of left staples is formed on the second surgical site,
wherein a distance between a cutting section of the surgical site and the first right stapling line the nearest to the cutting section in the rightward direction is greater than another distance between the cutting section and the first left stapling line the nearest to the cutting section in the leftward direction in order to obtain an object area for pathological examination, which is not damaged by staples, from the first surgical site; and
an indicator configured to indicate a position of the one or more rows of right staple discharge holes, and arranged at a right side of the cutter guide for indicating an asymmetry of the surgical linear stapler; further comprising a plurality of members arranged at a predetermined interval along the lengthwise direction of the staple cartridge between the cutter guide and a first row of right staple discharge holes the most adjacent to the cutter guide in a rightward direction, and configured to press and hold a tissue area near the cutting section when the surgical site is cut.

10. A surgical linear stapler comprising:
a staple cartridge configured to be internally loaded with staples for stapling a surgical site
an anvil configured to form the staples discharged from the staple cartridge;
a cutter configured to move along a lengthwise direction of the staple cartridge by external force and to cut the surgical site stapled by the staples;
a pressing member configured to press and discharge the staples toward the outside of the staple cartridge;
wherein the staple cartridge comprises a cutter guide for guiding the cutter to move along the lengthwise direction of the staple cartridge, and a cartridge body formed with one or more rows of left staple discharge holes and one or more rows of right staple discharge holes arranged at opposite sides of the cutter guide,
wherein the surgical site comprises a first surgical site to be removed by the cutter and a second surgical site to be remained in a human body,
wherein right stapling lines stapled by right staples loaded within the one or more rows of right staple discharge holes are formed on the first surgical site, and left stapling lines stapled by left staples loaded within the one or more rows of left staple discharge holes are formed on the second surgical site,
wherein the right stapling lines and the left stapling lines are asymmetrically arranged with respect to a cutting section of the surgical site; and
an indicator configured to indicate a position of the one or more rows of right staple discharge holes, and arranged at a right side of the cutter guide for indicating an asymmetry of the surgical linear stapler so that an object tissue for pathological examination is included in the first surgical site; further comprising a plurality of members arranged at a predetermined interval along the lengthwise direction of the staple cartridge between the cutter guide and a first row of right staple discharge holes the most adjacent to the cutter guide in a rightward direction, and configured to press and hold a tissue area near the cutting section when the surgical site is cut.

11. The surgical linear stapler according to claim 10, wherein a number of rows of left staples is greater than a number of rows of right staples.

12. The surgical linear stapler according to claim 10, wherein the right stapling lines comprise a first right stapling line the nearest to a cutting section of the surgical site and a second right stapling line the nearest to the first right stapling line in the rightward direction, and
wherein a distance between the cutting section and the first right stapling line is greater than another distance between the first right stapling line and the second right stapling line.

13. The surgical linear stapler according to claim 10, wherein the pressing member comprises right pressing members configured to press and discharge the right staples toward the outside of the one or more rows of right staple discharge holes and left pressing members configured to press and discharge the left staples toward the outside of the one or more rows of left staple discharge holes, and the right pressing members and the left pressing members are asymmetrically arranged with respect to the cutter guide, and
wherein the surgical linear stapler further comprises a driving wedge pushes up the right pressing member and the left pressing members toward the one or more rows of right staple discharge holes and the one or more rows of left staple discharge holes, respectively.

14. A surgical linear stapler comprising:
a staple cartridge configured to be internally loaded with staples for stapling a surgical site
an anvil configured to form the discharged staples from the staple cartridge;
a cutter configured to move along a lengthwise direction of the staple cartridge by external force and to cut the surgical site stapled by the staples;
a pressing member configured to press and discharge the staples toward the outside of the staple cartridge;
wherein the staple cartridge comprises a cutter guide for guiding the cutter to move along the lengthwise direction of the staple cartridge, and a cartridge body formed with one or more rows of left staple discharge holes and one or more rows of right staple discharge holes arranged at opposite sides of the cutter guide, wherein the surgical site comprises a first surgical site to be removed by the cutter and a second surgical site to be remained in a human body, and wherein right stapling lines stapled by right staples loaded within the one or more rows of right staple discharge holes are formed on the first surgical site, and the right stapling lines comprise a first right stapling line the nearest to a cutting section of the surgical site, and;

a plurality of members arranged at a predetermined interval along the lengthwise direction of the staple cartridge between the cutter guide and a first row of right staple discharge holes the most adjacent to the cutter guide in a rightward direction, and configured to press and hold a tissue area near the cutting section when the surgical site is cut, wherein the tissue area is placed between the cutting section and the first right stapling line.

15. A surgical linear stapler comprising:

a staple cartridge configured to be internally loaded with staples for stapling a surgical site an anvil configured to form the staples discharged from the staple cartridge;

a cutter configured to move along a lengthwise direction of the staple cartridge by external force and to cut the surgical site stapled by the staples;

a pressing member configured to press and discharge the staples toward the outside of the staple cartridge;

wherein the pressing member comprises right pressing members and left pressing members, wherein the right pressing members are placed at a first side of the cutter and the left pressing members are placed at opposite side of the right pressing member with respect to the cutter, wherein a dimension of the right pressing members is different from a dimension of the left pressing members, and wherein the difference between the dimension of the right pressing members and the dimension of the left pressing members makes an asymmetric stapling line for an object margin;

an indicator placed at a right side of the cutter among the surface of an end effector of the surgical linear stapler corresponding to a position of one or more rows of right staple discharge holes for indicating an asymmetry of the surgical linear stapler and visually informing an exact position of the surgical linear stapler to a user so that an object tissue for pathological examination is included in a first surgical site to be removed by the cutter, and a driving wedge pushes up the right pressing member and the left pressing members toward the one or more rows of right staple discharge holes and one or more rows of left staple discharge holes, respectively.

16. The surgical linear stapler according to claim 15, wherein a number of the right pressing members is fewer than a number of the left pressing members.

* * * * *